US010926529B2

(12) United States Patent
Chisena et al.

(10) Patent No.: US 10,926,529 B2
(45) Date of Patent: Feb. 23, 2021

(54) METHOD OF ADDITIVE MANUFACTURING AN INTERNAL WAVE SPARSE STRUCTURE WITH VARYING GEOMETRY FOR LOCALIZED TUNABLE STRUCTURAL PROPERTIES THROUGHOUT A PART

(71) Applicants: The Regents of the University of Michigan, Ann Arbor, MI (US); Stratasys, Inc., Eden Prairie, MN (US)

(72) Inventors: Robert Chisena, Ann Arbor, MI (US); Miguel Angel Funes Lora, Ann Arbor, MI (US); Albert Shih, Ann Arbor, MI (US); Darren Bolger, South Lyon, MI (US); Jeffrey Wensman, Ann Arbor, MI (US); Andrew Hanson, Saint Paul, MN (US); Gary Larson, Independence, MN (US); Chris Holshouser, Chanhassen, MN (US)

(73) Assignees: The Regents of the University of Michigan, Ann Arbor, MI (US); Stratasys, Inc., Eden Prairie, MN (US)

( * ) Notice: Subject to any disclaimer, the term of this patent is extended or adjusted under 35 U.S.C. 154(b) by 0 days.

(21) Appl. No.: 16/790,325

(22) Filed: Feb. 13, 2020

(65) Prior Publication Data

US 2020/0180298 A1 Jun. 11, 2020

Related U.S. Application Data

(62) Division of application No. 15/610,114, filed on May 31, 2017, now abandoned.

(51) Int. Cl.
*B33Y 80/00* (2015.01)
*B33Y 10/00* (2015.01)
(Continued)

(52) U.S. Cl.
CPC ............ *B33Y 80/00* (2014.12); *B29C 64/118* (2017.08); *B29C 64/386* (2017.08);
(Continued)

(58) Field of Classification Search
CPC ......... B33Y 80/00; B33Y 50/02; B33Y 10/00; B29D 99/0021; B29C 64/118
See application file for complete search history.

(56) References Cited

U.S. PATENT DOCUMENTS 2,677,906 A 5/1954 Reed
6,004,124 A 12/1999 Swanson et al.
(Continued)

OTHER PUBLICATIONS

Prosecution History from corresponding U.S. Appl. No. 15/610,114, filed May 31, 2017 including: Advisory Action dated Jan. 2, 2020; Final Rejection dated Oct. 17, 2019; and Non-Final Rejection dated Apr. 2, 2019.

*Primary Examiner* — Vincent H Tran
(74) *Attorney, Agent, or Firm* — Westman, Champlin & Koehler, P.A.

(57) ABSTRACT

Disclosed are three-dimensional parts, such as orthotics and prosthetics, having sinusoidal wave pattern infill structures first and second boundary walls. Also disclosed are printers or systems configured to manufacture such parts, as well as methods of manufacturing such parts. The sinusoidal wave pattern infill structures are formed between, and normal to, the first and second boundary walls and are configured to provide locally tunable structural properties in different regions of the part.

19 Claims, 7 Drawing Sheets

(51) Int. Cl.
    *B33Y 50/02*           (2015.01)
    *B29C 64/386*         (2017.01)
    *B29C 64/118*         (2017.01)
    *B29D 99/00*          (2010.01)
    *B33Y 30/00*          (2015.01)
    *B29L 31/00*          (2006.01)
    *A61F 2/76*           (2006.01)

(52) U.S. Cl.
    CPC .......... *B29D 99/0021* (2013.01); *B33Y 10/00* (2014.12); *B33Y 30/00* (2014.12); *B33Y 50/02* (2014.12); *A61F 2/76* (2013.01); *B29L 2031/7532* (2013.01)

(56) References Cited

U.S. PATENT DOCUMENTS

| | | |
|---|---|---|
| 6,722,872 B1 | 4/2004 | Swanson et al. |
| 7,063,285 B1 | 6/2006 | Turley et al. |
| 7,604,470 B2 | 10/2009 | LaBossiere et al. |
| 7,625,200 B2 | 12/2009 | Leavitt |
| 7,938,356 B2 | 5/2011 | Taatjes et al. |
| 8,403,658 B2 | 3/2013 | Swanson |
| 8,439,665 B2 | 5/2013 | Batchelder et al. |
| 8,985,497 B2 | 3/2015 | Mannella |
| 9,108,360 B2 | 6/2015 | Comb et al. |
| 9,073,263 B2 | 7/2015 | Mannella et al. |
| 9,327,447 B2 | 5/2016 | Batchelder et al. |
| 2016/0324261 A1 | 11/2016 | Guyan |
| 2018/0056607 A1* | 3/2018 | Socha-Leialoha .......................... G05B 19/4099 |
| 2018/0104912 A1* | 4/2018 | Bastian ................ B29C 64/386 |

* cited by examiner

METHOD OF ADDITIVE MANUFACTURING AN INTERNAL WAVE SPARSE STRUCTURE WITH VARYING GEOMETRY FOR LOCALIZED TUNABLE STRUCTURAL PROPERTIES THROUGHOUT A PART

This application is a divisional of U.S. patent application Ser. No. 15/610,114, filed on May 31, 2017 and entitled METHOD OF ADDITIVE MANUFACTURING AN INTERNAL WAVE SPARSE STRUCTURE WITH VARYING GEOMETRY FOR LOCALIZED TUNABLE STRUCTURAL PROPERTIES THROUGHOUT A PART

BACKGROUND

The present disclosure relates to 3D printers for printing or otherwise producing three-dimensional (3D) parts. In particular, the present disclosure relates to methods of printing compliant, thin-walled or shell structures having internal wave sparse structures to produce localized, tunable structural properties, such as stiffness, hardness, strength, energy absorption, damping, toughness, ductility, impact strength, thermal properties, or flow properties, throughout the part.

Additive manufacturing, also called 3D printing, is generally a process in which a three-dimensional (3D) object is built by adding material to form a 3D part rather than subtracting material as in traditional machining. Using one or more additive manufacturing techniques, a three-dimensional solid object of virtually any shape can be printed from a digital model of the object by an additive manufacturing system, commonly referred to as a 3D printer. A typical additive manufacturing work flow includes slicing a three-dimensional computer model into thin cross sections defining a series of layers, translating the result into two-dimensional position data, and feeding the data to a 3D printer which manufactures a three-dimensional structure in an additive build style. Additive manufacturing entails many different approaches to the method of fabrication, including fused deposition modeling, ink jetting, selective laser sintering, powder/binder jetting, electron-beam melting, electrophotographic imaging, and stereolithographic processes.

In a fused deposition modeling additive manufacturing system, a printed part is made from a digital representation of the printed part in an additive build style by extruding a flowable part material along toolpaths. The part material is extruded through an extrusion tip carried by a print head of the system and is deposited as a sequence of roads onto a substrate. The extruded part material fuses to previously deposited part material and solidifies upon a drop in temperature. In a system where the material is deposited in planar layers, the position of the print head relative to the substrate is incremented along an axis (perpendicular to the build plane) after each layer is formed, and the process is then repeated to form a printed part resembling the digital representation.

In fabricating printed parts by depositing layers of a part material, supporting layers or structures are typically built underneath overhanging portions or in cavities of printed parts under construction, which are not supported by the part material itself. A support structure may be built utilizing the same deposition techniques by which the part material is deposited. A host computer generates additional geometry acting as a support structure for the overhanging or free-space segments of the printed part being formed. Support material is then deposited pursuant to the generated geometry during the printing process. The support material adheres to the part material during fabrication, and is removable from the completed printed part when the printing process is complete.

Fused deposition modeling and other 3D printing technologies may be used to create thin-walled structures. Found extensively in nature and engineering, these thin-walled structures are particularly suited for efficiently transferring loads using minimal weight and material. For example, thin-walled structures are used in buildings, bridges, ships, warehouses, fluid flow systems, pressurized vessels, fluid transfer systems, aerospace shells and wings, automotive hoods and doors, and medical devices such as impact helmets, orthotics and prosthetics. These examples represent only some of the various thin-walled structures in use. The manner in which loads are transferred through thin-walled structures is the primary reason for their extensive use.

SUMMARY

An aspect of the present disclosure is directed to the use of sinusoidal wave pattern infill structures within thin-walled structures having first and second boundary walls. Another aspect of the present disclosure is directed to the use of wavy toolpath infill structures which are normal to the outer boundaries of the thin-walled structure, and is not limited to sinusoidal wave pattern infill structures. Discussions of sinusoidal wave pattern infill structures as illustrative embodiments are not intended exclude other wavy toolpath infill structures.

In exemplary embodiments, the sinusoidal wave pattern infill structures are formed between the first and second boundary walls and are configured to provide varying structural properties in different regions of the part. In exemplary embodiments, the sinusoidal wave pattern of the wave pattern infill structure is oriented normal to the boundary walls. Also, in exemplary embodiments, the sinusoidal wave pattern infill structure has variable properties, such as sinusoidal wave pattern amplitude, bead width, frequency, and interference, with at least one of the variable properties varied throughout the part to tune the structural properties in different regions of the part.

Another aspect of the present disclosure is directed to a method of additive manufacturing a three-dimensional part having a thin-walled structure. In the method, required structural properties for different regions of a part, such as an orthotic or a prosthetic, are determined or identified. Then, the part is printed to include first and second boundary walls, defining a contour of the part, and a sinusoidal wave pattern infill structure formed between the first and second boundary walls to provide the desired structural properties for the different regions of the part.

This Summary and the Abstract are provided to introduce a selection of concepts in a simplified form that are further described below in the Detailed Description. This Summary is not intended to identify key features or essential features of the claimed subject matter.

Definitions

Unless otherwise specified, the following terms as used herein have the meanings provided below:

The terms "preferred", "preferably", "example" and "exemplary" refer to embodiments of the invention that may afford certain benefits, under certain circumstances. However, other embodiments may also be preferred or exemplary, under the same or other circumstances. Furthermore, the recitation of one or more preferred or exemplary embodiments does not imply that other embodiments are not useful, and is not intended to exclude other embodiments from the scope of the present disclosure.

Directional orientations such as "above", "below", "top", "bottom", and the like are made with reference to a layer-printing direction of a 3D part. In the embodiments shown below, the layer-printing direction is the upward direction along the vertical z-axis. In these embodiments, the terms "above", "below", "top", "bottom", and the like are based on the vertical z-axis. However, in embodiments in which the layers of 3D parts are printed along a different axis, such as along a horizontal x-axis or y-axis, the terms "above", "below", "top", "bottom", and the like are relative to the given axis. Further, other coordinate systems can be used. For example, while a base coordinate system can be defined, for example by a build plate or platen, layers can be printed at an angle (e.g., 45°) normal to the build plate (between the x-axis or y-axis and the z-axis).

The term "providing", such as for "providing a material", when recited in the claims, is not intended to require any particular delivery or receipt of the provided item. Rather, the term "providing" is merely used to recite items that will be referred to in subsequent elements of the claim(s), for purposes of clarity and ease of readability.

Unless otherwise specified, temperatures referred to herein are based on atmospheric pressure (i.e. one atmosphere).

The terms "about" and "substantially" are used herein with respect to measurable values and ranges due to expected variations known to those skilled in the art (e.g., limitations and variabilities in measurements).

The terms "structural property", "structural properties", "mechanical property", or "mechanical properties" are used herein to refer to measurable physical characteristics of a structure that include but are not limited to stiffness, hardness, strength, energy absorption, specific damping, toughness, ductility, impact strength, thermal properties, or flow properties or any measurable or expected variations known to those skilled in the art.

The terms "sinusoidal wave pattern", "sinusoidal wave infill pattern", and "wavy toolpath infill pattern" are used herein to refer to curved wave patterns and infill structures which have, for individual layers or portions of layers, smooth continuous paths with repetitive oscillations.

The terms "locally tuned" and "locally tunable" are used herein to refer to the control or establishment of structural properties or mechanical properties in different regions of a 3D part by varying properties of a sinusoidal or other wavy toolpath infill pattern or structure.

DETAILED DESCRIPTION

The present disclosure is directed to 3D printing apparatus and methods of using a wave infill technique to improve manufacturing efficiency and to tune the mechanical properties throughout a printed part, such as custom orthotics and prosthetics.

In preparation of a design for 3D printing using known techniques, each sliced layer in a digital model may be assigned an infill pattern. The infill pattern may be uniform throughout a part, or may be assigned for each layer. Two types of infill patterns are common: (1) direction-parallel infills that use short, parallel line-segments to fill the interior of an outer part contour; and (2) contour infills that continuously offset the outer part contour to fill the interior. The density of material of each layer can be altered by varying the space between these line segments, thus creating infills that may range from be sparse, to moderate, to fully dense.

With the commonly-used infill modes such as direction-parallel infill and contour infill, the weight of the printed structure is not optimized, and tailoring of structural bending stiffness about certain anatomical axes are difficult to quantify and reproduce. These known infill modes are also found to be inefficient in the manufacturing of thin-walled structures.

The present invention recognizes limitations in the prior art infill modes and offers a wave infill approach that increases manufacturing speed while providing a capability to locally tune structural part properties. In the case of custom orthotics and prosthetics, these devices need to be manufactured quickly, with minimal weight, and with specific structural properties to ensure improved patient outcomes. Locally tuning the structural properties of high impact cranial helmets or automotive components that will alter the impulse and force directions around delicate or sensitive regions are other examples.

Figure 1:
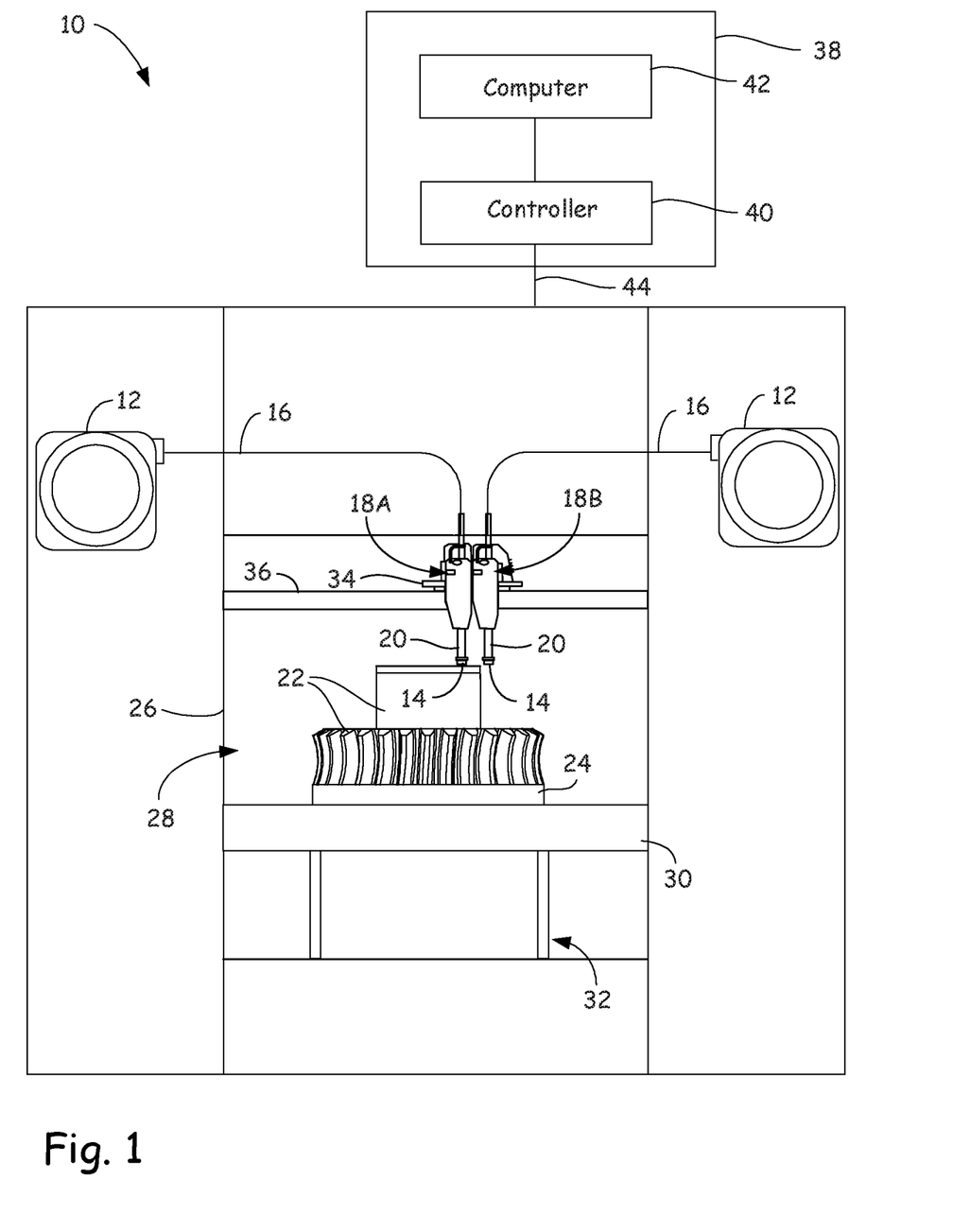
FIG. 1 is a front view of a 3D printer configured to print 3D parts and support structures in accordance with exemplary embodiments.

The wave infill techniques and methods of the present disclosure may be used with any suitable additive manufacturing system, commonly referred to as a 3D printer. For example, FIG. 1 illustrates a 3D printer 10 that has a substantially horizontal print plane where the part being printed is indexed in a substantially vertical direction as the part is printed in a layer-by-layer manner using at least one print head. For example, in FIG. 1, 3D printer 10 includes two print heads 18A, 18B and two consumable assemblies 12, where each consumable assembly 12 is an easily loadable, removable, and replaceable container device that retains a supply of a consumable filament for printing with system 10. Typically, one of the consumable assemblies 12 contains a part material filament, and the other consumable assembly 12 contains a support material filament, each supplying filament to one print head 18A or 18B. However, both consumable assemblies 12 may be identical in structure. Each consumable assembly 12 may retain the consumable filament on a wound spool, a spool-less coil, or other supply arrangement, such as discussed in Swanson et al., U.S. Pat. No. 8,403,658; Turley et al. U.S. Pat. No. 7,063,285; Taatjes at al., U.S. Pat. No. 7,938,356; and Mannella et al., U.S. Publication Nos. 8,985,497 and 9,073,263.

Each print head 18A and 18B is an easily loadable, removable and replaceable device comprising a housing that retains a liquefier assembly 20 having a nozzle tip 14. Each print head 18A and 18B is configured to receive a consumable material, melt the material in liquefier assembly 20 to produce a molten material, and deposit the molten material from a nozzle tip 14 of liquefier assembly 20. Examples of suitable liquefier assemblies for print head 18 include those disclosed in Swanson et al., U.S. Pat. No. 6,004,124; LaBossiere, et al., U.S. Pat. No. 7,604,470; Leavitt, U.S. Pat. No. 7,625,200; and Batchelder et al., U.S. Pat. No. 8,439,665. Other suitable liquefier assemblies include those disclosed in Batchelder et al., U.S. Pat. No. 9,327,447.

Guide tube or feed tube 16 interconnects consumable assembly 12 and print head 18A or 18B, where a drive mechanism of print head 18A or 18B (or of 3D printer 10) draws successive segments of the consumable filament from consumable assembly 12, through guide tube or feed tube 16, to liquefier assembly 20 of print head 18A or 18B. In this embodiment, guide or feed tube 16 may be a component of 3D printer 10, rather than a sub-component of consumable assemblies 12. In other embodiments, guide tube 16 is a sub-component of consumable assembly 12, and may be interchanged to and from 3D printer 10 with each consumable assembly 12. During a build operation, the successive segments of consumable filament that are driven into print head 18A or 18B are heated and melted in the liquefier assembly 20. The melted material is extruded through nozzle tip 14 in a layer wise pattern to produce printed parts.

Exemplary 3D printer 10 is an additive manufacturing system for printing 3D parts or models and corresponding support structures (e.g., 3D part 22 and support structure 24) from the part and support material filaments, respectively, of consumable assemblies 12, using a layer-based, additive manufacturing technique. Suitable additive manufacturing systems for 3D printer 10 include fused deposition modeling systems developed by Stratasys, Inc., Eden Prairie, Minn. under the trademark "FDM."

As shown, 3D printer 10 includes system housing 26, chamber 28, platen 30, platen gantry 32, head carriage 34, and head gantry 36. System housing 26 is a structural component of system 10 and may include multiple structural sub-components such as support frames, housing walls, and the like. In some embodiments, system housing 26 may include container bays configured to receive consumable assemblies 12. In alternative embodiments, the container bays may be omitted to reduce the overall footprint of 3D printer 10. In these embodiments, consumable assembly 12 may stand proximate to printer 10, while providing sufficient ranges of movement for guide or feed tubes 16 and print heads 18 that are shown schematically in FIG. 1.

Chamber 28 is an environment that contains platen 30 for printing 3D part 22 and support structure 24. Chamber 28 may provide an enclosed heated environment (e.g., with circulating heated air) to reduce the rate at which the part and support materials solidify after being extruded and deposited (e.g., to reduce distortions and curling). In alternative embodiments, chamber 28 may be omitted and/or replaced with different types of build environments. For example, 3D part 22 and support structure 24 may be built in a build environment that is open to ambient conditions or may be enclosed with alternative structures (e.g., flexible curtains). Platen 30 is a platform on which 3D part 22 and support structure 24 are printed in a layerwise manner, and is supported by platen gantry 32. Platen gantry 32 is a gantry assembly configured to move platen 30 along (or substantially along) the vertical z-axis.

Head carriage 34 is a unit configured to receive and retain one or both print heads 18A and 18B, and is supported by head gantry 36. Head carriage 34 preferably retains each print head 18A and 18B in a manner that prevents or restricts movement of the print head 18 relative to head carriage 34 so that nozzle tip 14 remains in the x-y build plane, but allows nozzle tip 14 of the print head 18 to be controllably moved out of the x-y build plane through movement of at least a portion of the head carriage 34 relative the x-y build plane (e.g., servoed, toggled, or otherwise switched in a pivoting manner).

In the shown embodiment, head gantry 36 is a robotic mechanism configured to move head carriage 34 (and the retained print heads 18A and 18B) in (or substantially in) a horizontal x-y plane above platen 30. Examples of suitable gantry assemblies for head gantry 36 include those disclosed in Swanson et al., U.S. Pat. No. 6,722,872; and Comb et al., U.S. Pat. No. 9,108,360, where head gantry 36 may also support deformable baffles (not shown) that define a ceiling for chamber 28. Head gantry 36 may utilize any suitable bridge-type gantry or robotic mechanism for moving head carriage 34 (and the retained print heads 18), such as with one or more motors (e.g., stepper motors and encoded DC motors), gears, pulleys, belts, screws, robotic arms, and the like.

In an alternative embodiment, platen 30 may be configured to move in the horizontal x-y plane within chamber 28, and head carriage 34 (and print heads 18A and 18B) may be configured to move along the z-axis. Other similar arrangements may also be used such that one or both of platen 30 and print heads 18A and 18B are moveable relative to each other. Platen 30 and head carriage 34 (and print heads 18A and 18B) may also be oriented along different axes. For example, platen 30 may be oriented vertically and print heads 18A and 18B may print 3D part 22 and support structure 24 along the x-axis or the y-axis.

3D printer 10 also includes controller assembly 38, which may include one or more control circuits (e.g., controller 40) and/or one or more host computers (e.g., computer 42) configured to monitor and operate the components of 3D printer 10. For example, one or more of the control functions performed by controller assembly 38, such as performing move compiler functions, can be implemented in hardware, software, firmware, and the like, or a combination thereof; and may include computer-based hardware, such as data storage devices, processors, memory modules, and the like, which may be external and/or internal to 3D printer 10. The disclosed methods of additive manufacturing thin-walled structures with wave pattern infill can be implemented, in full or in part, by configuration of components of controller assembly 38 to control 3D printer 10 to utilize the disclosed techniques.

Controller assembly 38 may communicate over communication line 44 with print heads 18A and 18B, chamber 28 (e.g., with a heating unit for chamber 28), head carriage 34, motors for platen gantry 32 and head gantry 36, and various sensors, calibration devices, display devices, and/or user input devices. In some embodiments, controller assembly 38 may also communicate with one or more of platen 30, platen gantry 32, head gantry 36, and any other suitable component of 3D printer 10. While illustrated as a single signal line, communication line 44 may include one or more electrical, optical, and/or wireless signal lines, which may be external and/or internal to 3D printer 10, allowing controller assembly 38 to communicate with various components of 3D printer 10.

During operation, controller assembly 38 may direct platen gantry 32 to move platen 30 to a predetermined height within chamber 28. Controller assembly 38 may then direct head gantry 36 to move head carriage 34 (and the retained print heads 18A and 18B) around in the horizontal x-y plane above chamber 28. Controller assembly 38 may also direct print heads 18A and 18B to selectively draw successive segments of the consumable filaments from consumable assemblies 12 and through guide or feed tubes 16, respectively.

While FIG. 1 illustrates a 3D printer 10 where a build plane is in a substantially horizontal x-y plane and the platen 30 is moved in a z direction substantially normal to the substantially horizontal x-y build plane, the present disclosure is not limited to a 3D printer 10 as illustrated in FIG. 1.

In exemplary embodiments, controller assembly 38 is configured to direct print heads 18A and 18B along pre-defined toolpaths to print three-dimensional thin-walled structures or parts. Thin-walled structures carry external loads through membrane forces parallel to the mid-surface between the first and second boundary walls of the structure. This structural behavior is referred to as membrane action. In the presence of a bending load, the structure furthest from the mid-surface, or neutral axis, resists the majority of the load while the material at the neutral axis remains completely free of load. For this reason, when designing compliant thin-walled structures with high load-to-weight ratios and whose primary load case is bending, material furthest from the mid-surface is the most important. Commonly-used thin-walled structures prone to bending and that require light-weighting utilize this important mechanism. For example, I-beams, corrugated sheets, and sandwich structures move material further from the mid-surface to reduce weight while maintaining the required structural properties of the part. However, due to the added complexity of these designs, the increased cost of conventional manufacturing methods limit the use of these lightweight structures.

Another strategy of thin-walled part design is to use the internal structure of the part to alter the structural properties of the part. For example, distributing material strategically throughout a part to stiffen certain regions and make others flexible can produce an internal loading pattern that causes a known deflection given a certain load. A structure that makes specific use of its locally tuned structure to achieve desired reactions given its interaction with its environment is called a compliant structure. These compliant structures provide simpler alternatives to moving joints that utilize the structure of the part to achieve a certain end-goal. Although the manufacturing of these types of structures is nearly impossible with conventional subtractive or molding techniques, additive manufacturing provides a method to add near-infinite complexity to the structure of a part with little additional cost.

In additive manufacturing, a part is sliced into layers and an infill pattern for each layer is assigned. To design a part that can be additive manufactured efficiently, is lightweight and can have locally tuned structural properties, internal wave sparse structures can be used to infill the interior of the thin-walled structure. These thin-walled structures have first and second boundary walls and a wave infill structure formed between and in contact with the boundary walls. The configuration of controller assembly 38 to direct the print heads along pre-defined wave toolpaths allows print times for the structures to be significantly reduced, particularly using sinusoidal or other wavy toolpath infill structures which require fewer changes of print direction, eliminating abrupt turns, and allow more continuous printing. Further, by controlling the properties of the wave infill structure, varying stiffness or other structural and mechanical properties can be achieved in different regions of the parts. The sinusoidal wave and other wavy toolpath infill structures, and the methods of manufacturing or printing parts including such structures, are described below in greater detail.

Figure 2:
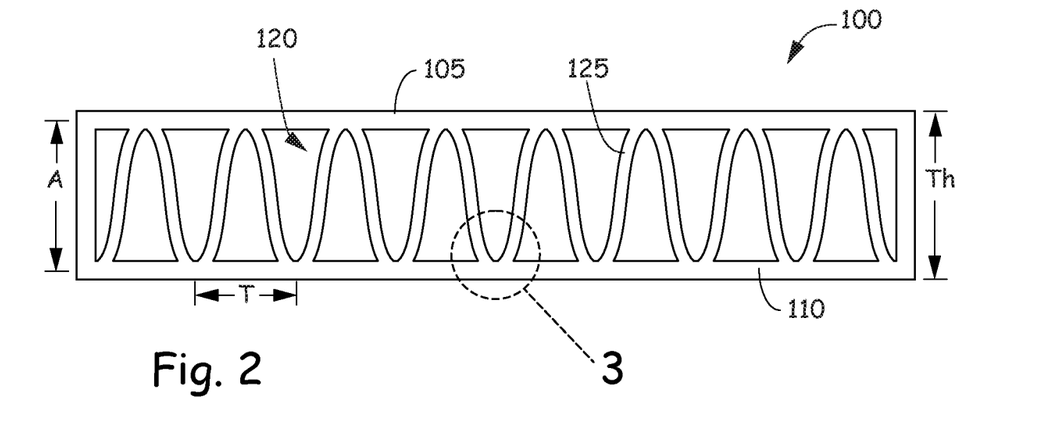
FIGS. 2 and 3 are diagrammatic illustrations of a portion of a printed part, having a wave infill structure, showing properties of the infill structure which can be selected or varied.

Referring now to FIG. 2, shown is a portion of a part 100 printed using disclosed printers and methods. The part 100 includes a thin-walled structure having first and second boundary walls 105 and 110 which define the contour or shape of at least a portion of the part. While shown as planar or flat walls, boundary walls 105 and 110 will typically have curvature. Part 100 also includes a wave pattern infill structure 120 formed between, and in contact with, boundary walls 105 and 110. In the exemplary embodiment, the wave pattern infill structure 120 is a sinusoidal wave pattern infill structure, though it need not be sinusoidal in all embodiments. The wave infill 125 for part 100, printed internally to the thin-walled structure layer-by-layer with boundary walls 105 and 110, is oriented normal to the outer contour of the layer. Thus, the wave infill structure 120 is maintained normal to the boundary walls throughout the layers.

Figure 3:
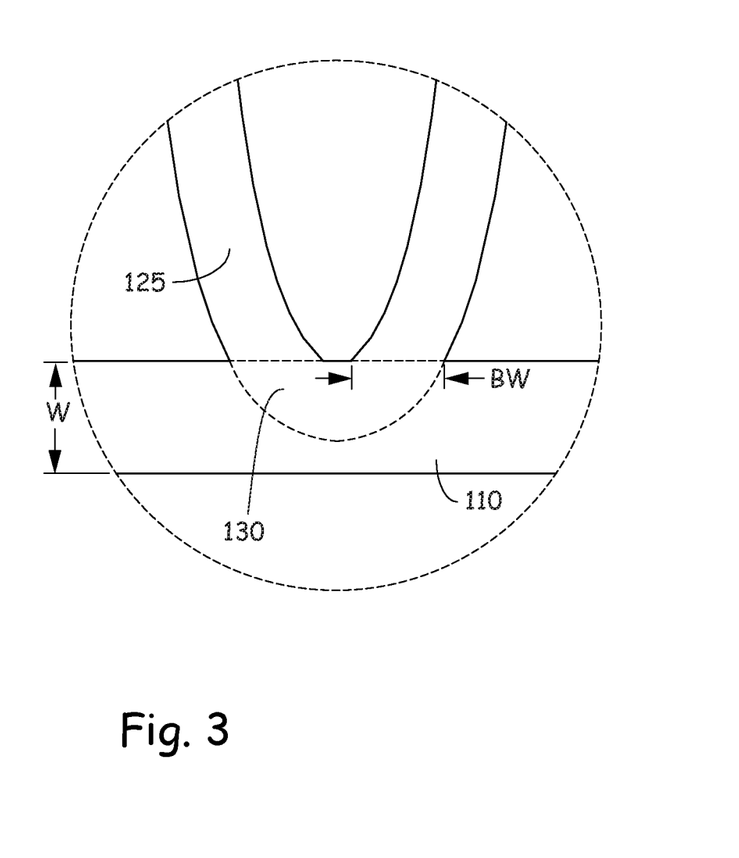
Figure 4:
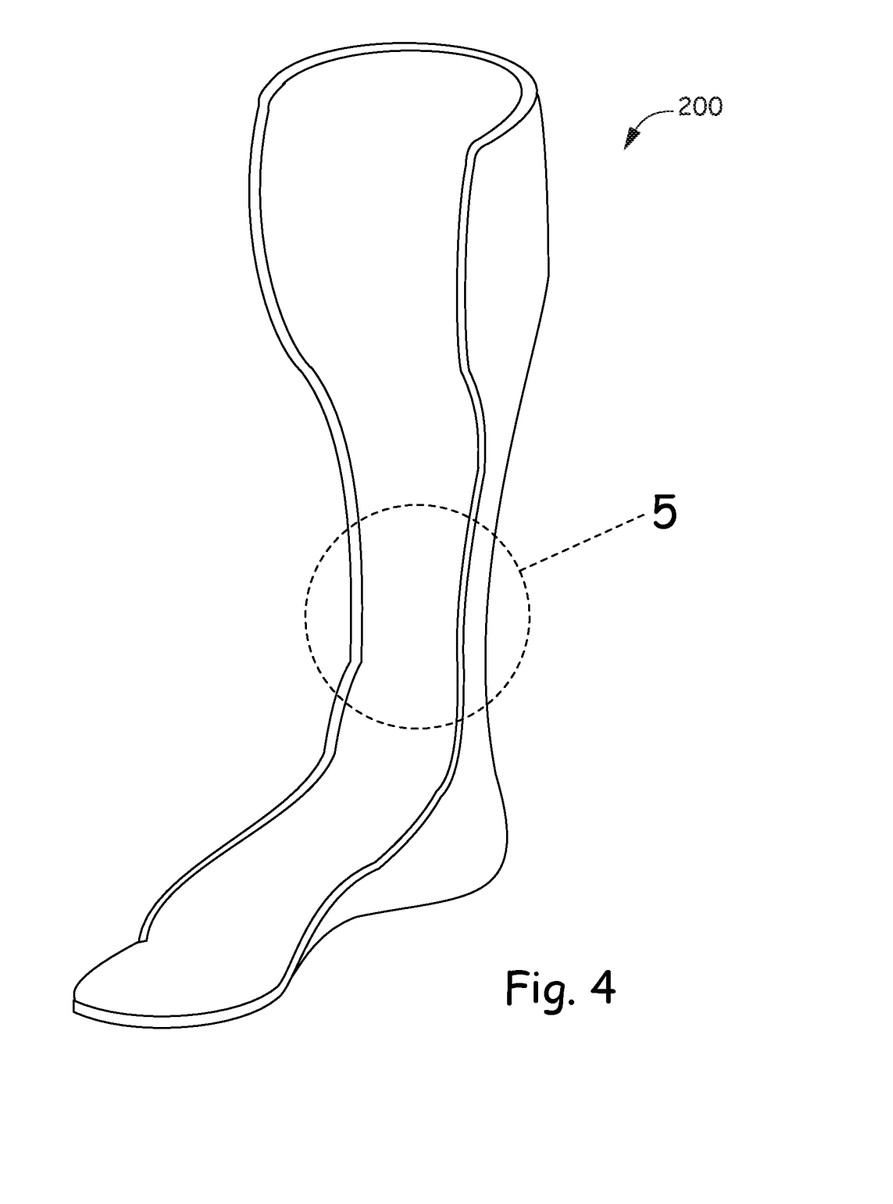
FIG. 4 is a diagrammatic illustration showing a prosthetic part which can be printed using the disclosed concepts and methods to have tuned properties.

In order to control structural or mechanical properties (e.g., stiffness) of the part 100, and allow the structural or mechanical properties to vary or be tailored in different regions of the part, one or more variable properties of the part and infill structure 120 can be varied throughout the part. FIG. 3 illustrates a portion of part 100 in greater detail, and FIGS. 2 and 3 together illustrate examples of such properties. As shown in FIGS. 2 and 3, part 100 has a thickness "Th" between outer surfaces of boundary walls 105 and 110 which must be selected. For the wave infill 125, the beadwidth "BW", the amplitude "A", and the period "T" indicative of frequency can also be controlled to tune the stiffness or other structural properties of the part in different regions. By controlling the amplitude and beadwidth of the wave infill 125, interference "I" (shown in interference region 130 in FIG. 3) between the boundary walls 105 and 110 and the infill 125 can also be controlled. Interference can be expressed as a percentage of the width "W" of a boundary wall overlapped by wave infill 125. Further, bead width and frequency can be used to adjust the inter-layer structural properties, as well.

Using stiffness as an example structural property, while varying these parameters, the structural stiffness of the thin-walled structure of part 100 can be altered from the material's inherent stiffness value to a lower value. Therefore, in some exemplary embodiments, it can be important to choose an FDM material with an inherent stiffness above the desired stiffness for any region of the part, and then the parameters of the wave infill can be controlled to achieve lower stiffness regions. In other embodiments, the structural stiffness of the thin-walled structure can be altered to a higher value.

In some exemplary embodiments, the thickness of the part 100 can either be a defined value or can be set depending on the loading requirements. Upon determination of the thickness, the frequency and amplitude of the wave infill can be set for different regions of the part. Frequency, or the radians of the sine wave per length, defines the waviness of the internal fill pattern of infill structure 120, and thus the density of the fill pattern. Amplitude is determined using an interference parameter, which as discussed above can be defined as percentage of overlap between the wave infill 125 and the outer contour or boundary walls 105 and 110. This interference defines the joint strength between the wave and the outer contour. High interferences produce high joint strengths but impacts surface quality at some point; whereas low interferences produce low joint strengths with unaffected surface quality. Finally, the bead width BW is set which defines the thickness of the extruded bead. The bead width affects the final part weight and the strength of the joints and overall structure.

Figure 5:
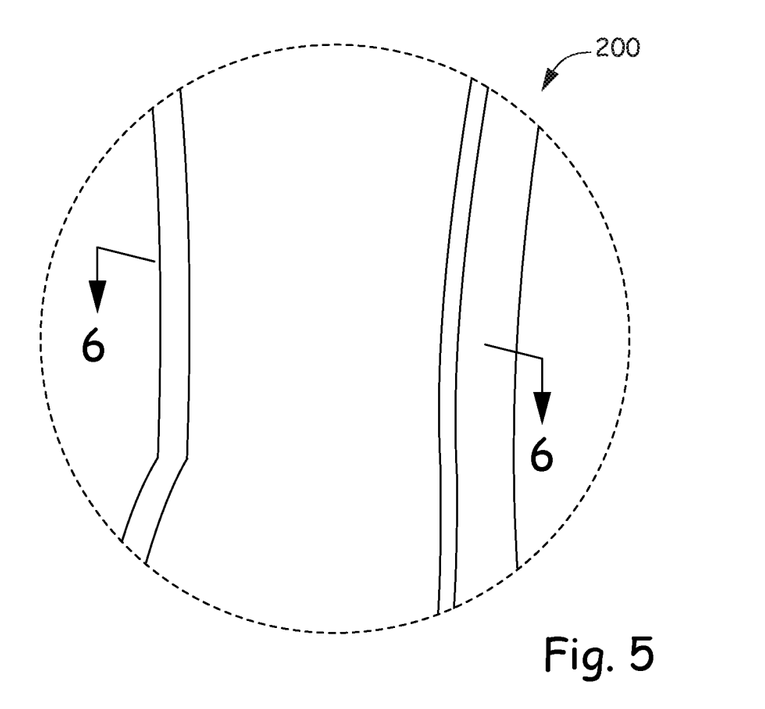
FIG. 5 is a diagrammatic illustration of a portion of the prosthetic part shown in FIG. 4.
Figure 6:
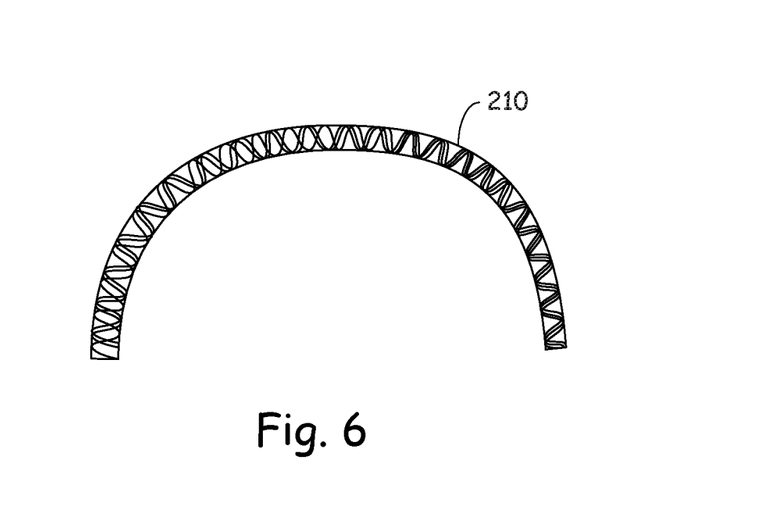
FIG. 6 is a cross section of the portion of the part shown in FIG. 5, illustrating toolpaths for various layers having a sinusoidal wave infill structure in accordance with an exemplary embodiment.

Furthermore, the waviness from layer-to-layer and within each layer of part 200 is, in some exemplary embodiments, generated such that there are no discontinuities in the wave in any direction. FIG. 5 illustrates a portion of part 200, along which a cross section 210 is shown in FIG. 6. In the cross section 210, shown is a set of layers (or toolpaths for layers) with continuously varying wave infill. As shown, the set of wave infill layers has small offsets between toolpaths in subsequent layers, which allows for efficient manufacture and continuously varying stiffness or other properties throughout the part, as well as avoiding the use of a support material which would otherwise be needed if abrupt, large offsets were used from one layer to the next. The technique of continuously altering the waviness throughout the part allows for continuous stiffness or property mapping that can be determined a priori with a numerical solving procedure. By adjusting the above variables within their respective design ranges, a range of structural stiffness can be attained and mapped from the numerical solver to the actual part.

Figure 7:
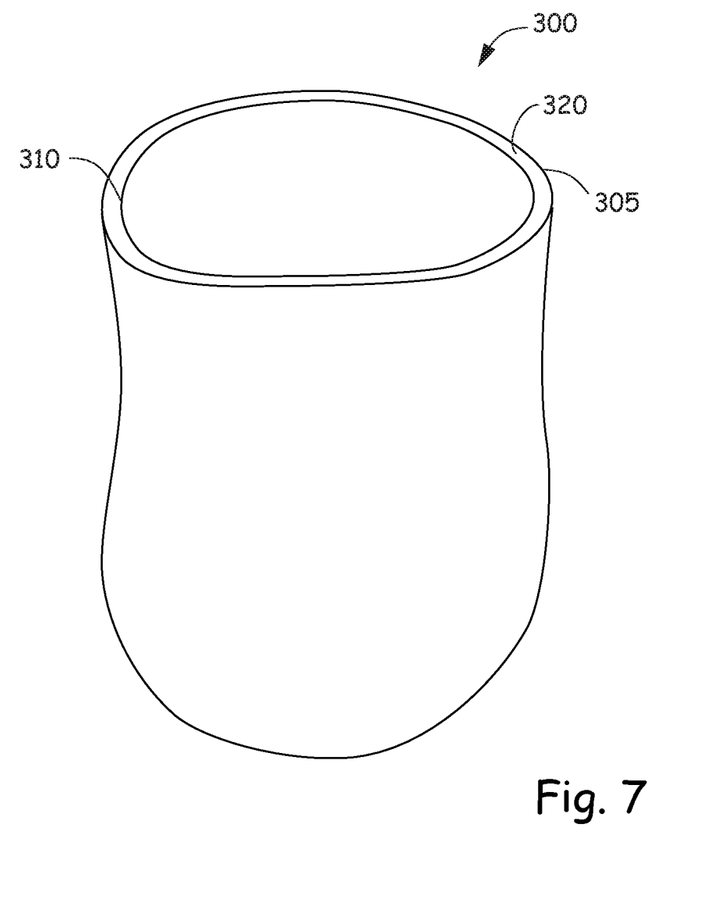
FIG. 7 is a perspective view of a prosthetic socket having a sinusoidal wave infill structure in accordance with another exemplary embodiment.
Figure 8:
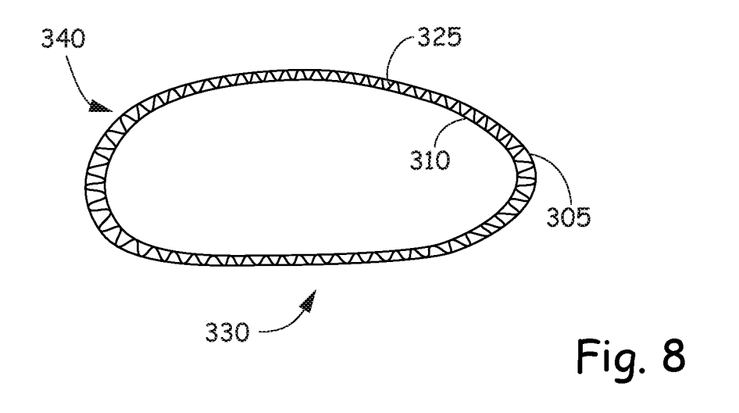
FIG. 8 is a diagrammatic top view showing the varying frequency of the sinusoidal wave infill structure of a prosthetic socket of FIG. 7.

As another example, FIG. 7 illustrates part 300, in the form of a prosthetic socket, which can be printed using disclosed printers and methods. Part 300 includes outer and inner boundary or contour walls 305 and 310, and a sinusoidal or other wavy toolpath infill pattern structure 320 between the walls. The wave infill pattern 325 of structure 320 for one layer of part 300 is shown in FIG. 8. As illustrated, the frequency of the wave infill pattern 325 is varied, as part of a continuous pattern defining a toolpath for the layer, between lower frequency regions, such as region 330, and higher frequency regions, such as region 340. This allows stiffness or other properties of part 300 to be varied in different regions of the part. As noted, other variables of the wave infill pattern, such as interference, can also be varied for this purpose.

In printing wave infill patterns for thin-walled parts, toolpaths are generated for each layer of the part, including wave portions of the toolpaths. Toolpaths including sinusoidal wave infill patterns, or other wavy infill patterns, result in more continuous movement of the print heads, reducing the time to print each layer and the overall part. In generating the wave infill portions of the toolpaths, a steering function can be used to maintain the alignment of the infill pattern throughout the layers of the part. The steering function ensures that the beadwidths of subsequent layers "stack" upon one another. Generally, an overlap of at least approximately 50% between beadwiths of adjacent layers is beneficial or required to avoid unsupported print regions in a layer.

Disclosed embodiments can utilize wave infill in the additive manufacturing of various types of thin-walled structures, including custom orthotics and prosthetics as described. These devices frequently rely heavily on a contact surface that mimics the shape of a portion of the body, such as of the foot and ankle, or of a prosthetic limb. Using optimization techniques, the required thickness and infill density of the part can be determined for various regions of the orthotic or prosthetic. For instance, posterior leaf spring orthotic designs require a large, tailored deflection in the sagittal plane to correct symptoms such as foot drop. The part thickness and internal wave infill characteristics can be tailored to achieve this deflection. Furthermore, a low frequency wave infill can be used in the strap location, for instance, where the part should have a low bending stiffness, to allow the patient to easily tighten the orthotic to his or her limb.

As discussed, using non-periodic sinusoidal wave infill for thin-walled structures allows printed parts to have specifically designed strengths, stiffnesses, weights or other characteristics. By varying parameters such as (1) bead width, (2) thickness, (3) frequency, and (4) interference, these characteristics can be tuned for specific uses, while still reducing print times for the part by allowing toolpaths which deposit layers in a continuous manner while maximizing the velocity of the print head(s). By performing mechanical testing on printed parts that vary these four parameters, the effect on structural stiffness, strength, layer print time, and weight of the sparse wave infill can be optimized for a given thin-walled structure. Other factors can also be optimized, such as which frequencies of the sine wave infill reduce the amount of vibration compared to typical direction-parallel raster infills. Using data from such testing, computer modeling, for example with an artificial neural network or other modeling techniques, can be used to model the relationship between input variables and resulting structural properties or other responses. The modeled relationships can then be used in optimizing selection of the variable parameters of the sinusoidal wave infill and generating toolpaths for printing the layers of a part.

For example, to determine the appropriate wave infill that will provide the desired structural properties, such as stiffness, in an orthotic part, a finite element analysis (FEA) model can be generated to model the stiffness of wave infill in an example simple geometry part. The FEA results for stiffness of the part can then be optimized for considerations such as reducing the weight of the part or reducing the build time of the part. Once the wave infill is optimized, the toolpaths for the part can be generated for each layer.

Figure 9:
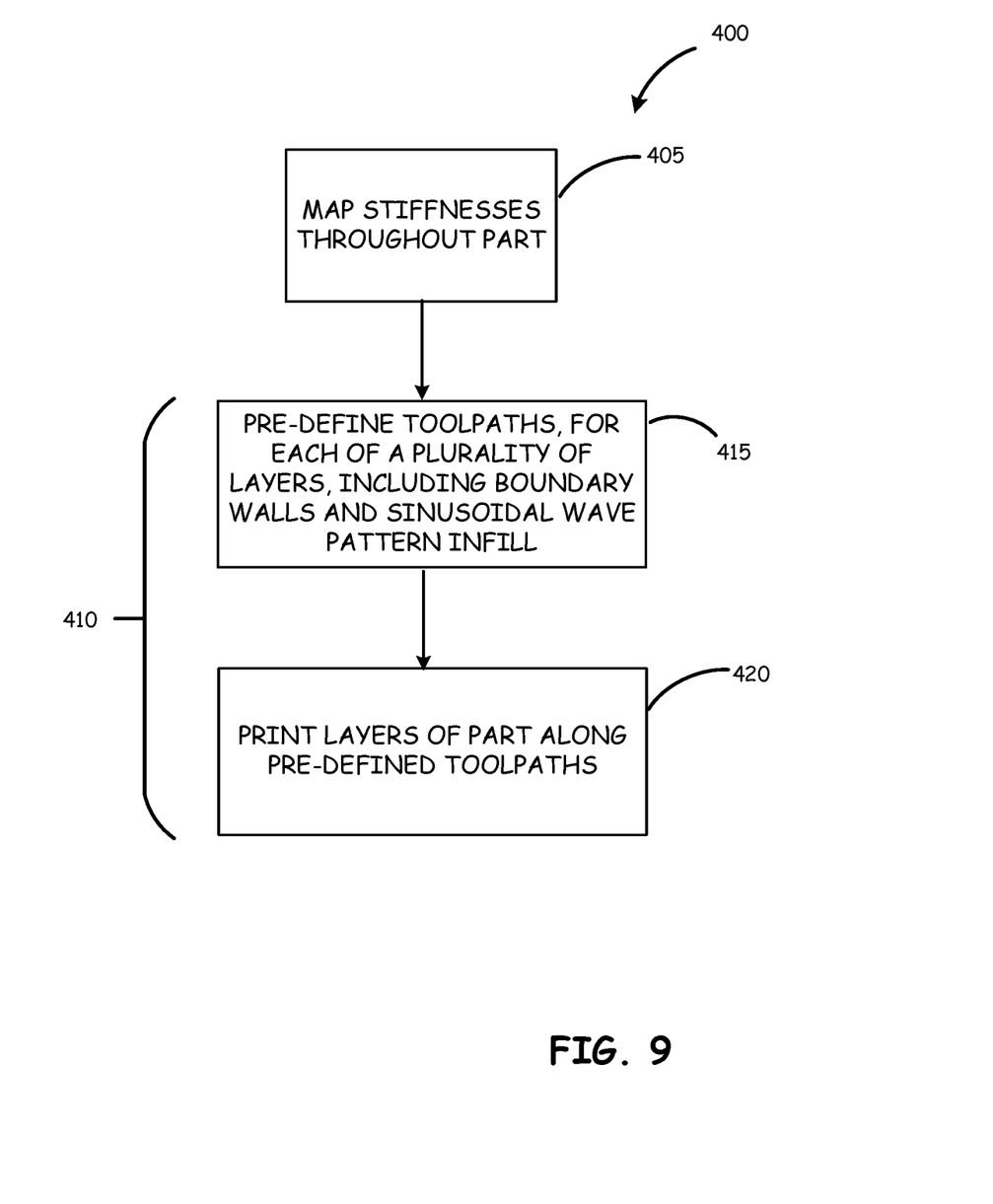
FIG. 9 is a flow diagram illustrating a method of additive manufacturing a three-dimensional part, having a thin walled structure, in accordance with some exemplary embodiments.

Methods of printing or additive manufacturing three-dimensional thin-walled parts have been described with reference to the exemplary embodiments of FIGS. 2-8. FIG. 9 is a flow diagram illustrating an example embodiment of such a method. As shown in method 400, in an initial step or steps 405, stiffness for different regions of the part to be manufactured are determined and mapped. Then in a step 410, the part is printed to include the first and second boundary walls which define the contour of the part, and to include a sinusoidal wave pattern infill structure formed between the first and second boundary walls. As discussed, the sinusoidal wave pattern infill structure is oriented normal to the boundary walls and has at least one varying property, such as frequency, beadwidth, interference, or amplitude/thickness, which is varied throughout the part to provide the desired stiffness for the different regions.

Also, as discussed, step 410 of printing the part includes, in exemplary embodiments, a step 415 of determining or pre-defining toolpaths for each of the layers of the part, and a step 420 of printing the layers of the part using the pre-defined toolpaths. Each layer includes portions of the first and second boundary walls and of the sinusoidal wave pattern infill structure. In exemplary embodiments, the pre-defined toolpath for each layer includes a non-interrupted toolpath for the sinusoidal wave pattern infill structure portion of the layer. This decreases print time for each layer and for the part.

Figure 10:
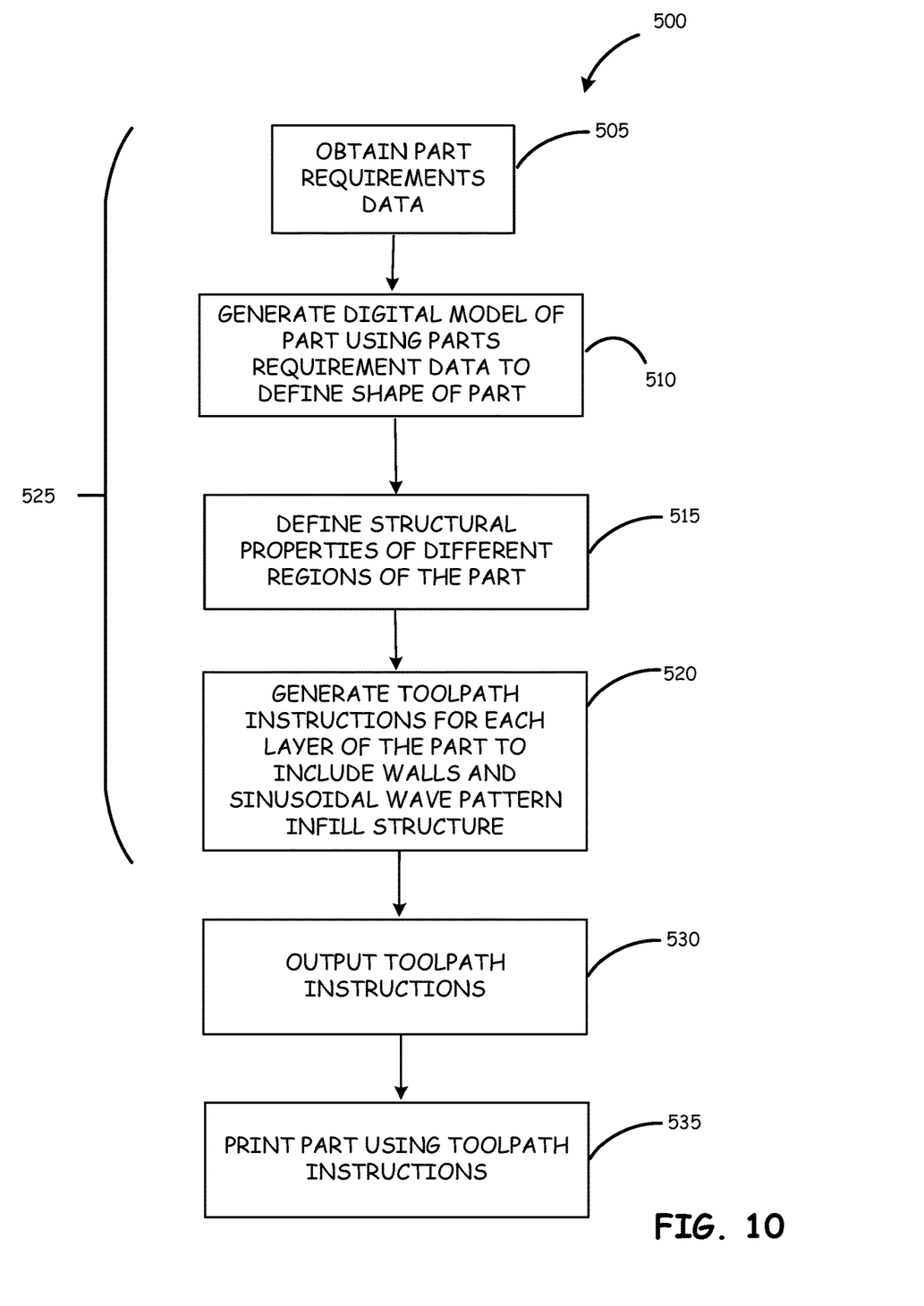
FIG. 10 is a flow diagram illustrating another embodiment of a method of additive manufacturing or printing a three-dimensional part in accordance with exemplary embodiment.

Referring now to FIG. 10, shown is another exemplary method 500 of printing a three-dimensional part, such as a custom prosthetic or orthotic for a patient, with an additive manufacturing system. The method of printing the three-dimensional part includes steps 525 which result in the generation of toolpath instructions required to print the part using the sinusoidal wave pattern infill as described above. The steps 525 form a method which improves the technological process of toolpath generation, and thus improves the function of a computer performing the steps to generate the toolpath instructions. While the computer of controller assembly 38 can be configured with computer readable instructions to implement these steps, the steps can also be implemented in one or more different computers, with the toolpath instructions stored, outputted or transmitted for use by controller assembly 38 to print the part using 3D printer 10.

Referring more specifically to the steps shown in FIG. 10, at step 505 parts requirements data is obtained for the part to be printed. In the case of a custom prosthetic or orthotic for a patient, obtaining the part requirements data can include obtaining measured or scanned data for the patient. For example, the obtained data can include information such as patient size and shape measurements, weight, etc. Next, at step 510, the method includes generating a digital model of the three-dimensional part using the part requirements data. The digital model defines the shape and dimensions of the three-dimensional part. At step 515, the structural property requirements of the part to be printed are defined for different regions of the part. For example, regions of the part which require more or less stiffness and strength are identified, and the required properties for these regions are defined.

Next, at step 520, the toolpath instructions for each layer of the three-dimensional part are generated. The toolpath instructions define the toolpaths for each layer required to print the part with the first and second boundary walls which define the part contour, and with a sinusoidal wave pattern infill structure formed between the boundary walls to provide the required structural properties for the different regions. As discussed above, this allows both tuning of the properties in different regions of the part, and decreased print times since the sinusoidal waveform toolpaths allow more continuous printing without starting and stopping to abruptly change directions. Once the toolpath instructions are generated at step 520, the instructions can be output at step 530, for example by being saved on a computer storage medium or transmitted for use in printing the part. Finally, at step 535, the three-dimensional part is printed using the generated toolpath instructions.

Although the present disclosure has been described with reference to preferred embodiments, workers skilled in the art will recognize that changes may be made in form and detail without departing from the spirit and scope of the disclosure. For example, while embodiments are illustrated showing non-periodic sinusoidal or other waveform infill structures, in some embodiments, the sinusoidal waveform infill structures can have varying amplitudes to vary the interference between the infill structure and the boundary walls. Other such alternative parameters can be varied instead. Also, while exemplary embodiments are illustrated for manufacturing orthotics or prosthetics, disclosed structures and methods are not limited to these types of printed parts. Also, disclosed concepts and methods can be used to print parts using any material that can be used to provide the desired structural properties, such as plastics, filled plastics, metals, etc., or with combinations of such materials.

The invention claimed is:

1. A method for printing a three-dimensional part with an additive manufacturing system, the method comprising:
    obtaining part requirements data for the three-dimensional part;
    generating a digital model of the three-dimensional part using the part requirements data, the digital model defining a shape of the three-dimensional part;
    defining required structural properties of different regions of the three-dimensional part;
    generating toolpath instructions for each of a plurality of layers of the three-dimensional part such that the three-dimensional part includes first and second boundary walls, defining a contour of the part, and a sinusoidal wave pattern infill structure formed between the first and second boundary walls to provide the required structural properties for the different regions of the part, and
    wherein generating the toolpath instructions for each of the plurality of layers further comprises generating a predefined non-interrupted toolpath for the sinusoidal wave pattern infill structure portion of the layer, wherein at least one property of the sinusoidal wave pattern infill structure is varied to provide the required structural properties for the different regions of the part.

2. The method of claim 1, wherein generating the toolpath instructions for each of the plurality of layers further comprises generating the toolpath instructions such that the sinusoidal wave pattern infill structure has a wave pattern at an orientation normal to the first and second boundary walls.

3. The method of claim 1, wherein the at least one property which is varied to provide the required structural properties for the different regions of the part comprises at least one of a sinusoidal wave pattern amplitude corresponding to part thickness, a beadwidth of the sinusoidal wave pattern infill structure, a frequency of the sinusoidal wave pattern infill structure, and interference of the sinusoidal wave pattern infill structure with the first and second boundary walls.

4. The method of claim 3, wherein the at least one property which is varied to provide the required structural properties for the different regions of the part comprises the frequency of the sinusoidal wave pattern infill structure.

5. The method of claim 1, and further comprising:
    outputting the toolpath instructions for each of a plurality of layers of the three-dimensional part; and
    printing the three-dimensional part using the toolpath instructions with the additive manufacturing system.

6. The method of claim 1, wherein the three-dimensional part is an orthotic or prosthetic part for a patient, and wherein obtaining part requirements data for the three-dimensional part further comprises obtaining measured or scanned data for the patient.

7. A method for printing a three-dimensional part with an additive manufacturing system, the method comprising:
    obtaining part requirements data for the three-dimensional part;
    generating a digital model of the three-dimensional part using the part requirements data, the digital model defining a shape of the three-dimensional part;

defining required structural properties of at least a first region and a second region of the three-dimensional part; and generating toolpath instructions for each of a plurality of layers of the three-dimensional part such that the three-dimensional part includes first and second boundary walls, defining a contour of the part, and a sinusoidal wave pattern infill structure formed between the first and second boundary walls to provide different structural properties to at least the first and second regions of the three-dimensional part, wherein generating the toolpath instructions for each of the plurality of layers further comprises generating the toolpath instructions for the at least first and second regions such that at least one property of the sinusoidal wave pattern infill structure is varied to provide the required structural properties for the different regions of the part, wherein the at least one property which is varied to provide the required structural properties for the different regions of the part comprises at least one of a sinusoidal wave pattern amplitude corresponding to part thickness, a beadwidth of the sinusoidal wave pattern infill structure, a frequency of the sinusoidal wave pattern infill structure, and interference of the sinusoidal wave pattern infill structure with the first and second boundary walls.

8. The method of claim 7, wherein generating the toolpath instructions for each of the plurality of layers further comprises generating the toolpath instructions such that the sinusoidal wave pattern infill structure has a wave pattern at an orientation normal to the first and second boundary walls in the at least first region and the second region.

9. The method of claim 7, wherein the at least one property which is varied to provide the required structural properties for the different regions of the part comprises the frequency of the sinusoidal wave pattern infill structure.

10. The method of claim 7, and further comprising:
outputting the toolpath instructions for each of a plurality of layers of the three-dimensional part; and
printing the three-dimensional part using the toolpath instructions with the additive manufacturing system.

11. The method of claim 7, wherein the three-dimensional part is an orthotic or prosthetic part for a patient, and wherein obtaining part requirements data for the three-dimensional part further comprises obtaining measured or scanned data for the patient.

12. The method of claim 11, wherein generating the toolpath instructions for each of the plurality of layers further comprises generating the toolpath instructions such that the sinusoidal wave pattern infill structure has a wave pattern at an orientation normal to the first and second boundary walls in the at least first region and the second region.

13. The method of claim 11, and further comprising:
outputting the toolpath instructions for each of a plurality of layers of the three-dimensional part; and
printing the three-dimensional part using the toolpath instructions with the additive manufacturing system.

14. A method for printing a three-dimensional part with an additive manufacturing system, the method comprising:
obtaining part requirements data for the three-dimensional part;
generating a digital model of the three-dimensional part using the part requirements data, the digital model defining a shape of the three-dimensional part;

defining required structural properties of at least a first region and a second region of the three-dimensional part; and generating toolpath instructions for each of a plurality of layers of the three-dimensional part such that the three-dimensional part includes first and second boundary walls, defining a contour of the part, and a sinusoidal wave pattern infill structure formed between the first and second boundary walls to provide different structural properties to at least the first and second regions of the three-dimensional part by varying a frequency of the sinusoidal wave pattern infill structure, wherein generating the toolpath instructions for each of the plurality of layers further comprises generating a predefined non-interrupted toolpath for the sinusoidal wave pattern infill structure portion of the layer.

15. A method for printing a three-dimensional part with an additive manufacturing system, the method comprising:
obtaining part requirements data for the three-dimensional part;
generating a digital model of the three-dimensional part using the part requirements data, the digital model defining a shape of the three-dimensional part;
defining required structural properties of different regions of the three-dimensional part;
generating toolpath instructions for each of a plurality of layers of the three-dimensional part such that the three-dimensional part includes first and second boundary walls, defining a contour of the part, and a sinusoidal wave pattern infill structure formed between the first and second boundary walls to provide the required structural properties for the different regions of the part, and
wherein generating the toolpath instructions for each of the plurality of layers further comprises generating a predefined non-interrupted toolpath for the sinusoidal wave pattern infill structure portion of the layer, wherein a frequency of the sinusoidal wave pattern infill structure is varied to provide the required structural properties for the different regions of the part.

16. The method of claim 15, wherein generating the toolpath instructions for each of the plurality of layers further comprises generating the toolpath instructions such that the sinusoidal wave pattern infill structure has a wave pattern at an orientation normal to the first and second boundary walls.

17. The method of claim 15, wherein the at least one other property of the sinusoidal wave pattern is varied to provide the required structural properties for the different regions of the part comprises at least one of a sinusoidal wave pattern amplitude corresponding to part thickness, a beadwidth of the sinusoidal wave pattern infill structure, and interference of the sinusoidal wave pattern infill structure with the first and second boundary walls.

18. The method of claim 15, and further comprising:
outputting the toolpath instructions for each of a plurality of layers of the three-dimensional part; and
printing the three-dimensional part using the toolpath instructions with the additive manufacturing system.

19. The method of claim 18, wherein the three-dimensional part is an orthotic or prosthetic part for a patient, and wherein obtaining part requirements data for the three-dimensional part further comprises obtaining measured or scanned data for the patient.

* * * * *

UNITED STATES PATENT AND TRADEMARK OFFICE
CERTIFICATE OF CORRECTION

PATENT NO. : 10,926,529 B2
APPLICATION NO. : 16/790325
DATED : February 23, 2021
INVENTOR(S) : Chisena et al.

It is certified that error appears in the above-identified patent and that said Letters Patent is hereby corrected as shown below:

In the Specification

Column 1, Line 13, please insert the following Government Support Clause:
--GOVERNMENT FUNDING
This invention was made with government support under FA8650-12-2-7230 awarded by the U.S. Department of the Air Force. The government has certain rights in the invention.--

Signed and Sealed this
Eighth Day of March, 2022

Drew Hirshfeld
*Performing the Functions and Duties of the
Under Secretary of Commerce for Intellectual Property and
Director of the United States Patent and Trademark Office*